(12) United States Patent
Luthi et al.

(10) Patent No.: US 8,250,783 B2
(45) Date of Patent: Aug. 28, 2012

(54) MULTI-COMPONENT FOOTBEDS

(75) Inventors: Simon M. Luthi, Lake Oswego, OR (US); Glen D. Hinshaw, Scottsdale, AZ (US); Joseph F. McMillan, Portland, OR (US); Peter C. Rueegger, Portland, OR (US); Michael Steszyn, Portland, OR (US)

(73) Assignee: Esoles LLC, Scottsdale, AZ (US)

( * ) Notice: Subject to any disclaimer, the term of this patent is extended or adjusted under 35 U.S.C. 154(b) by 976 days.

(21) Appl. No.: 12/180,528

(22) Filed: Jul. 26, 2008

(65) Prior Publication Data

US 2009/0071038 A1 Mar. 19, 2009

Related U.S. Application Data

(63) Continuation-in-part of application No. 11/857,186, filed on Sep. 18, 2007.

(51) Int. Cl.
*A43B 7/14* (2006.01)
*A43B 13/38* (2006.01)
(52) U.S. Cl. .................... 36/44; 36/91; 36/155
(58) Field of Classification Search ............... 36/91, 88, 36/43, 44, 155–159
See application file for complete search history.

(56) References Cited

U.S. PATENT DOCUMENTS

| | | | |
|---|---|---|---|
| 3,084,695 A | 4/1963 | O'Donnell | |
| 4,813,157 A * | 3/1989 | Boisvert et al. | 36/44 |
| 4,841,648 A * | 6/1989 | Shaffer et al. | 36/43 |
| 5,237,520 A | 8/1993 | White | |
| 5,799,414 A * | 9/1998 | Kellerman | 36/44 |
| 5,832,634 A | 11/1998 | Wong | |
| 6,000,147 A * | 12/1999 | Kellerman | 36/44 |
| 6,205,685 B1 * | 3/2001 | Kellerman | 36/44 |
| 7,210,250 B2 * | 5/2007 | Gallegos | 36/44 |
| 7,392,559 B2 | 7/2008 | Peterson | |
| 7,484,319 B2 * | 2/2009 | Cheskin et al. | 36/44 |
| 7,644,522 B2 * | 1/2010 | Ramirez | 36/160 |
| 7,665,169 B2 * | 2/2010 | Cheskin et al. | 12/146 B |
| 7,908,768 B2 * | 3/2011 | Cheskin et al. | 36/44 |
| 2002/0138923 A1 | 10/2002 | Shaffeeullah | |
| 2004/0194344 A1 * | 10/2004 | Tadin | 36/44 |
| 2006/0080869 A1 * | 4/2006 | Johnson | 36/155 |
| 2006/0247892 A1 | 11/2006 | Peterson | |
| 2007/0039205 A1 | 2/2007 | Erb et al. | |
| 2007/0043582 A1 | 2/2007 | Peveto et al. | |
| 2007/0180632 A1 * | 8/2007 | Gallegos | 12/146 B |
| 2009/0049712 A1 * | 2/2009 | Steszyn et al. | 36/91 |

FOREIGN PATENT DOCUMENTS

| | | |
|---|---|---|
| FR | 2406434 | 5/1979 |
| FR | 2838308 A1 | 10/2003 |
| WO | WO9852435 | 11/1998 |
| WO | 037124 A1 | 5/2003 |
| WO | 2008036398 A2 | 3/2008 |
| WO | 2008080137 A1 | 7/2008 |

OTHER PUBLICATIONS

Search Report and Written Opinion for PCT/US2008/076366 dated Feb. 24, 2009.

* cited by examiner

*Primary Examiner* — Marie Patterson
(74) *Attorney, Agent, or Firm* — George A. Herbster

(57) ABSTRACT

A method and apparatus for supplying a customer with a footbed. A kiosk provides measurements of a consumer's feet with a self-guided display by using both pressure measurements and scanning of the feet. The measurement information is converted to identify which of the preselected and stocked components proximate the kiosk can be combined to provide an appropriate footbed for the consumer.

10 Claims, 18 Drawing Sheets

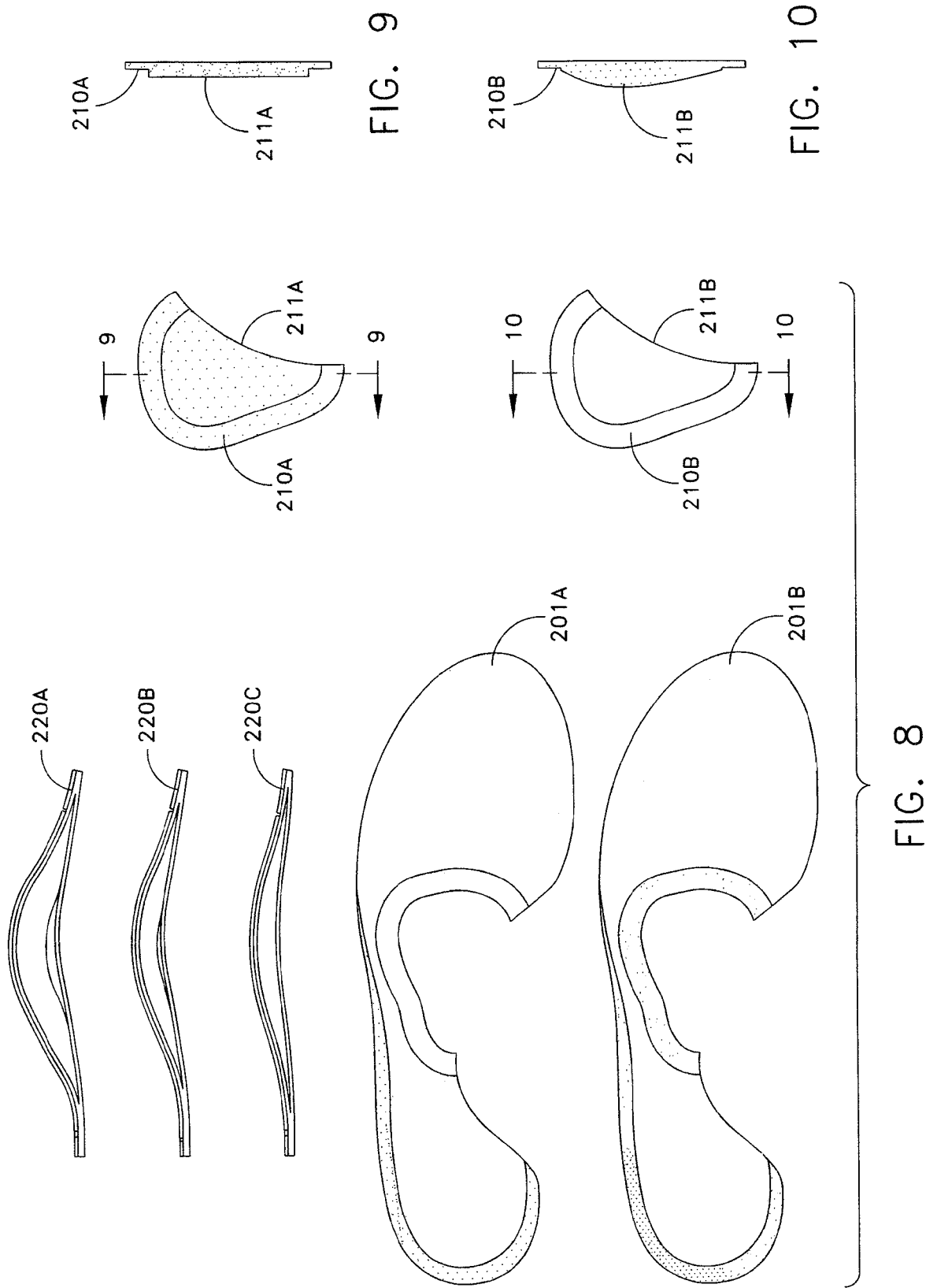

COMPONENT INVENTORY

| Sizes | 3.5 | 4 | 4.5 | 5 | 5.5 | 6 | 6.5 | 7 | 7.5 | 8 | 8.5 | 9 | 9.5 | 10 | 10.5 | 11 | 11.5 | 12 | 12.5 | 13 |
|---|---|---|---|---|---|---|---|---|---|---|---|---|---|---|---|---|---|---|---|---|
| Base | B1 | | B2 | | B3 | | B4 | | B5 | | B6 | | B7 | | B8 | | B9 | | B10 | |
| Arch | | A1 | | | | A2 | | | | A3 | | | | A4 | | | | A5 | | |
| Met Head | | M1 | | | | M2 | | | | M3 | | | | M4 | | | | M5 | | |

FIG. 11

MULTI-COMPONENT FOOTBEDS

CROSS REFERENCE TO RELATED APPLICATION

This application is a continuation-in-part of U.S. patent application Ser. No. 11/857,186 filed Sep. 18, 2007 for Footbeds and a Method and Apparatus for Producing Such Footbeds, which application is assigned to the same assignee as this invention.

BACKGROUND OF THE INVENTION

1. Field of the Invention

This invention generally relates to foot orthotics and more specifically the delivery to a consumer of footbeds that take into account several criteria including the plantar surface topography of each of the consumer's feet.

2. Description of Related Art

Over the years many companies have endeavored to produce a footbed that provides improved support for a consumer's foot. Each method involves two basic phases, namely: a measurement phase and a production-delivery phase. The measurement phase involves a use of apparatus for obtaining meaningful measurements of the foot, particularly the topography of the plantar surface. The production-delivery phase involves the conversion of the results of the measurement phase into physical footbeds and the delivery of the finished footbeds to the consumer.

In the gold standard and dominant methodology used by medical personnel, the measurement phase requires the formation of a plaster cast and mold. A practitioner produces a plaster cast of each foot after manipulating each foot to the referenced neutral position subject to compensation for any observed anatomical deformities of that foot. The non-weight bearing condition exists when no forces are applied to the foot, as when the foot is suspended in air.

The production-delivery phase begins when the practitioner sends these casts to a laboratory. Laboratory personnel make a mold from the cast and then use personal, information, a priori knowledge of the practitioner's procedures and other experiences to modify the molds. Then laboratory personnel use each mold to form a corresponding orthotic block which is finished at the laboratory and returned to the practitioner as an orthotic footbed.

After receipt, the practitioner dispenses the orthotic footbed to the patient. If a patient reports only little or no relief or reports discomfort, the practitioner must reevaluate the patient. If changes to the orthotic footbed are required, then either the entire process must be repeated or the orthotic footbed must be sent back to the laboratory with instructions for additional corrections.

As will be apparent, the measurement phase for this approach requires professional personnel. Production and delivery occurs generally by transporting the foot model to a production facility and returning the orthotics to the practitioner. As a result while this approach produces a very good orthotic, it is costly and involves significant delays between the measurement phase and the completion of the production-delivery phase.

U.S. Pat. No. 7,392,559 (2008) and U.S. Patent Application Pub. No. US2006/0247892 (2006) to Peterson, and both assigned to the assignee of this invention, disclose an alternative method and apparatus for manufacturing custom footbeds corresponding in quality to those produced by the gold standard approach. During a measurement phase a scanner with an air cushion and related equipment produce a topographical map of the bottom of each foot while the foot is in a semi-weight bearing state and in the neutral position; i.e., a semi-weighted, supported, aligned position. The air cushion captures the foot in this position and measures the distances corresponding to the spacing between a reference plane and the bottom of the foot. A manufacturing facility converts these measurements into information by which a computer numerically controlled machine produces a custom orthotic insert.

This approach eliminates the need for producing and transporting a foot model to a manufacturing site. However, the measurement phase still requires professional personnel to position the consumer's foot on the scanner. The production-delivery phase still involves the time to manufacture and transport the footbeds to and from a central manufacturing site.

Consequently, while these footbeds are less expensive to manufacture than those by the gold standard, they are not economically feasible for use by a large number of consumers who have no significant foot abnormalities, but would benefit from such footbeds. To overcome this characteristic, several companies have developed systems with the expectation of providing a consumer with a shoe or footbed in which the costs involved with the measurement and production-delivery phases are minimized.

U.S. Pat. No. 5,237,520 (1993) to White discloses one such foot measurement and footwear sizing system. During a measurement phase, a consumer stands on a scanner at a retail store. The scanner derives three-dimensional topographical information about the consumer's feet. During the manufacturing-delivery phase, this three-dimensional information is processed to identify a matching manufactured footwear product that can be sent to a retail store for delivery to a customer. This shipment includes a last for use in subsequent manufacturing of custom footwear and footwear products at the retail store.

U.S. Patent Application Pub. No. 2007/0039205 (2007) to Erb et al. discloses two embodiments of a patient station or kiosk used during the measurement phase. In one, a foot measurement device is replicated on a floor and a vertical surface. In the other, the measuring device is on the floor only. Measurement devices include an optical scanner and a sensor for measuring pressure. Information derived from the measurement devices is converted into a shoe prescription that a store representative uses to construct a pair of shoes during the production-delivery phase. During this phase, additional structural adjustments to achieve consumer comfort may be necessary.

Erb et al. also disclose a method and system for identifying a kit of footwear components for assembly into customized footwear for a consumer. Specifically, the scanned foot measurements and other consumer provide a basis for printing a "prescription" by which a selection is made from a set of prefabricated footwear components.

U.S. Patent Application Pub. No. US2002/0138923 (2002) to Shaffeeullah discloses a method and apparatus for producing individually contoured shoe inserts at a local site. More specifically, at the local site a scanner generates data representative of the shape of the foot. This data is processed based upon characteristics of the consumer's foot, qualities the consumer desires and the manner in which the consumer walks. After the measurement phase ends, the modified data then transfers to a device for forming an insert by molding a blank template at the local site to produce a desired shape during the production-delivery phase. This system is disclosed as being operated by an individual other than the consumer. Although this system may minimize the time to complete the production-delivery phase, the replication of insert production apparatus at each local site can increase the production-delivery phase costs significantly.

The Erb et al. patent could reduce the time for and cost of the measurement and production-delivery phases. However, there is a possibility that the resulting custom footwear may not be acceptable to the consumer. Specifically, in this system the foot is not aligned and is not in a supported position when the scanning occurs. Rather, in the Erb et al. patent a system, preferably with a foam mat, deforms under the weight of the consumer. Thus scanning occurs when the foot is in a fully compensated position with the arch flattened and the foot elongated. Moreover, as feet generally are not symmetrical in the full compensated position because one foot may flatten more than the other so the feet are determined to be different sizes when, in fact, they are not.

Although a system in accordance with Erb et al. might eliminate the need for a professional during the measurement phase, there is recognition that a consumer may be directed eventually to a podiatrist or other professional. The time and costs for the production-delivery phase are reduced because the shoe is assembled at the retail store. However, the retail store must bear the additional costs for a large inventory of shoe lasts and other components in order to minimize delivery time. Further, the actual time and cost during this phase are somewhat uncertain because the consumer determines when the shoes are acceptable. This is a very subjective test.

The White patent and Shaffeeullah applications disclose systems that could minimize the time and costs of one phase. However, they do not minimize the time and costs for both phases.

International Publication No. WO98/52435 (1998) to McRoskey discloses adjustable orthotics comprising orthotically functional and interchangeable components. The interchangeable components are inserted into a main body after which a cover overlies the components.

U.S. Pat. No. 3,084,695 (1963) to O'Donnell discloses an arch supporting cushion inner sole. The inner sole has an intermediate sheet of sponge rubber having curved channels that define segmental areas. Selected pads are interposed between upper and lower plies whereby the pads form bulges at various areas.

U.S. Pat. No. 4,841,648 (1989) to Shaffer discloses a personalized insole kit. An insole has a surface that contains a plurality of shapes, each disposed for a specific correction. Each shape is contained on the surface of the insole by hooks and loops. The insole is marked to identify a correct location for each component. This patent specifically discloses an insole with an arch pad, a heel pad, a metatarsal pad and a corn/callous/lesion pad.

U.S. Pat. No. 5,832,634 (1998) to Wong discloses sports footwear with a sole unit that comprises at least one composite material layer partly involving the sole unit itself. Specifically the sole comprises at least one portion formed of woven composite material having a part positioned in correspondence with the metatarsal region of the user's foot and a part at a position corresponding to the arch region of the foot. The portion in the metatarsal region is flexible. The part in the plantar arch region is rigid.

The previously identified Erb et al. published application discloses footwear components selected from a plurality of pre-manufactured footwear components having substantially the same function, but having different physical attributes to accommodate different foot configurations. These include arch supports and heel pads.

In summary and as previously indicated, the Peterson published applications provide high quality orthotic footbeds. However, the costs, in time and expense, for each of the measurement and production-delivery phases are high and preclude its application to a major market. Other prior art approaches reduce the time and costs associated with some of these phases, but generally at a reduced quality, particularly in the quality of the information provided during the measurement phase.

For example, the Peterson patent and published application disclose measurements taken in a semi-weight bearing state. Measurement techniques that scan the feet under a full-weight bearing state can produce incorrect arch measurements. As will be apparent, arch height and length vary with weight. In a full-weight bearing state arch height is at a minimum and arch length is at a maximum. In a non-weight bearing state arch height is at a maximum and arch length is at a minimum. An intermediate and more accurate measurement occurs when the foot is in a semi-weight bearing state. Moreover, whereas the Peterson patent and published application disclose the use of an air cushion to capture a foot in a semi-weight bearing position; other references disclose full weight bearing with an attendant distortion on the bottom of the foot as the tissue spreads under weight.

What is needed is a system for providing method for producing footbeds for consumers in which a measurement occurs locally without the requirement for any professional assistance and yields accurate information about a consumer's feet. The system should identify an inner sole base member, an arch support and a metatarsal pad having appropriate properties based upon these measurements. The construction of a footbed should then be based upon a selected inner sole base member, arch support and metatarsal pad for easy assembly by the consumer from an inventory at the site thereby to further minimize the cost of footbeds, even though the quality of these footbeds approaches the quality of orthotic footbeds made by either the gold standard method or by the methods in the Peterson patent and published application.

SUMMARY

Therefore it is an object of this invention to provide a method and system for providing low cost, high quality footbeds to consumers.

Another object of this invention is to provide footbeds to consumers at a minimal cost.

Yet another object of this invention is to provide a method and apparatus for producing a footbed that the consumer can assemble.

Yet still another object of this invention is to provide a method and apparatus that enables the construction of a footbed with minimal costs associated with the measurement and production-delivery phases.

Still yet another object of this invention is to provide a measurement method and apparatus that can be used by a consumer without assistance.

In accordance with one aspect of this invention, a footbed is provided for a consumer's foot characterized by forefoot, rear foot, lateral and medial column, arch and metatarsal head areas. The footbed includes an insole base, a metatarsal pad insert and an arch support insert. The insole base is taken from a group of insole bases for underlying the forefoot and rear foot areas and portions of the lateral column area between the forefoot and rear foot areas. The insole base has at least one vacuity substantially coextensive with the areas underlying the arch and metatarsal head areas and portions of the medial column area. The metatarsal pad insert is taken from a group of metatarsal pad inserts of different properties. The arch support insert is taken from a group of arch support inserts of different properties. The inserts are attached to the insole base to span the vacuity and to provide support for the metatarsal head and arch areas of the foot, respectively.

In accordance with another aspect, this invention provides a method by which a consumer at a store can obtain a footbed with characteristics that are adapted for the consumer's feet. There is an inventory of footbed components at the store. They are organized into a plurality of groups, each with at least one subgroup. The components in each subgroup have certain characteristics. The consumer is guided through a measurement phase during which the consumer enters personal information into the system, generates a pressure map of both feet, generates a topographical map for each foot. The system then generates a list of one component from each subgroup for each foot. Thereafter the consumer gathers each component on the list from the inventory for assembly into footbeds.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 8 depicts a sample set of components for forming a footbed as shown in FIG. 5;

FIG. 9 is a cross-sectional view taken along lines 9-9 in FIG. 8;

FIG. 10 is a cross-sectional view taken along lines 17-17 in FIG. 8;

FIG. 11 is a chart that depicts a typical component inventory at a local site.

DESCRIPTION OF ILLUSTRATIVE EMBODIMENTS

Figure 1:
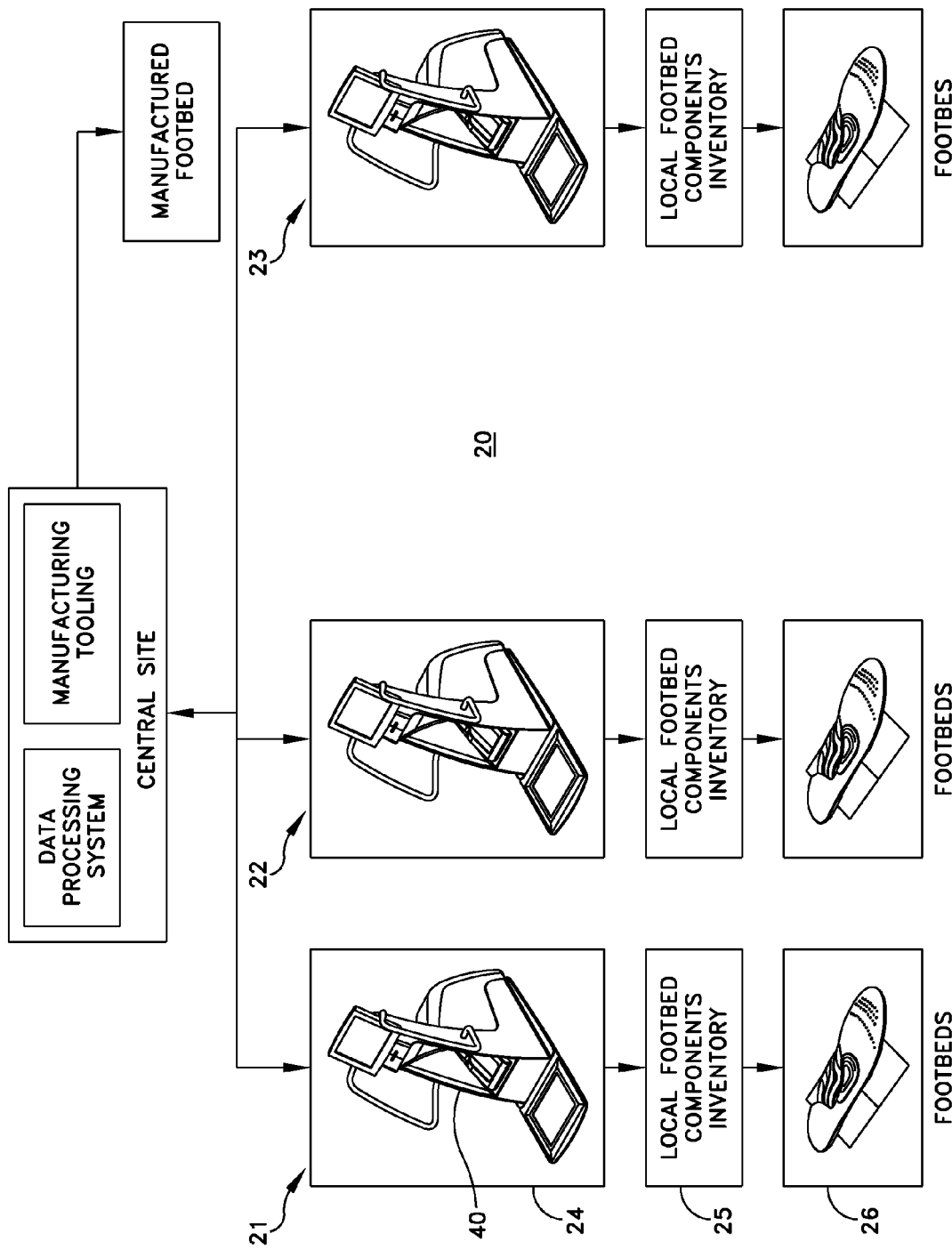
FIG. 1 is a pictorial representation of a network of local sites that include kiosks for enabling the assembly of footbeds in accordance with this invention.

The various objectives of this invention are achieved by increasing the efficiency of both the measurement phase and the production-delivery phase for providing a consumer with a set of footbeds adapted for the topography of the consumer's feet. FIG. 1 depicts a network 20 for producing footbeds in accordance with this invention that includes kiosks for performing the measurement phase at remote or local sites 21, 22 and 23, typically each at a different retail store. Site 21, as an example, includes a measurement station 24 and a local inventory of footbed components 25 from which individual components are selected for assembly into footbeds 26. The measurement station 24 provides information on which to base this selection of components.

Figure 2:
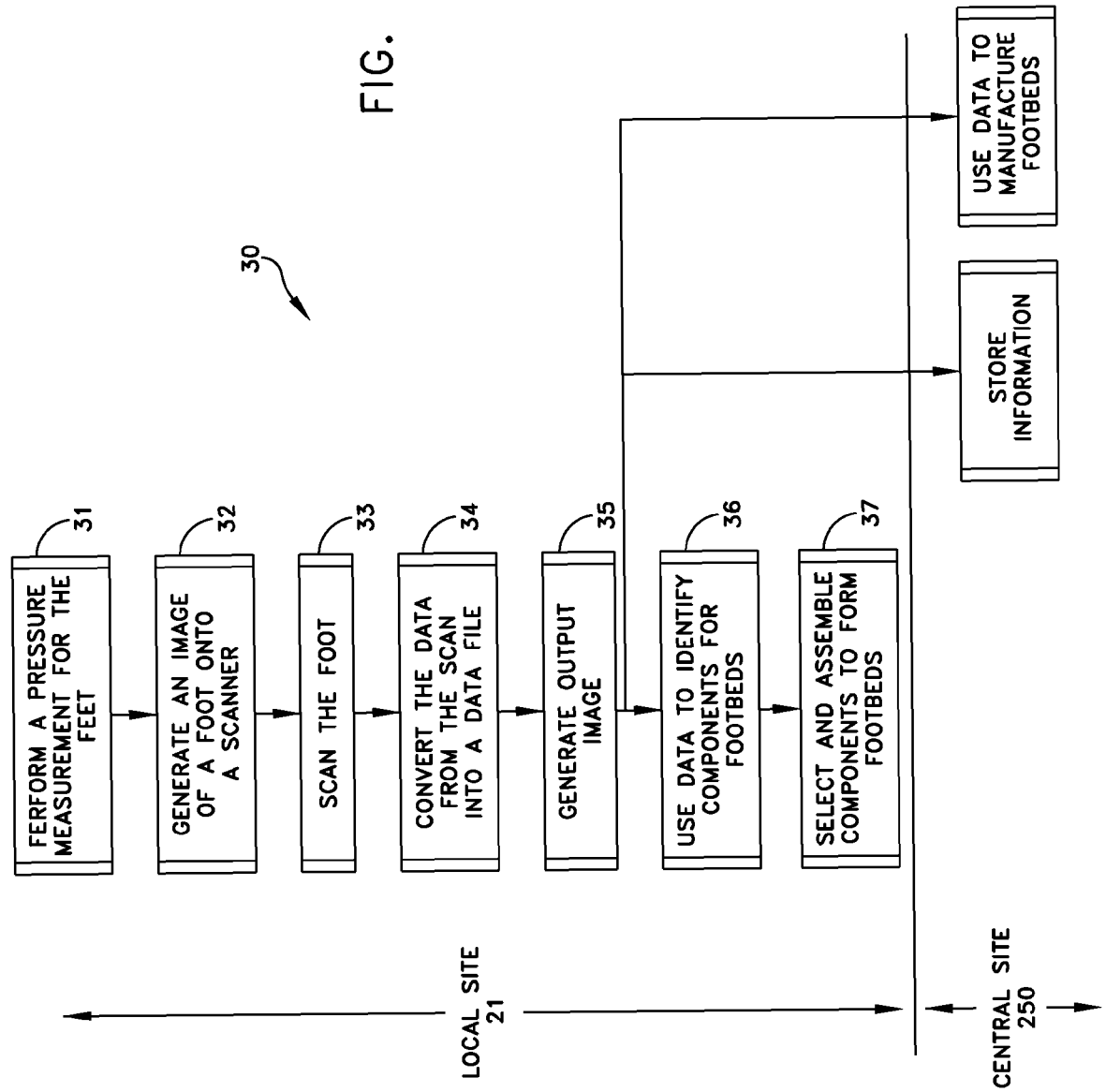
FIG. 2 is a functional diagram of operations that occur within the apparatus of FIG. 1.

As shown in FIG. 2, the operation 30 that constitutes the measurement phase includes a number of processes. A process 31 performs a pressure measurement of the consumer's feet for the purpose of generating an image of each foot. When that information has been obtained, process 32 projects an image of a foot onto equipment that captures the foot in a position essentially aligned with the projected foot image. Typically this equipment will include a scanner.

Next, the consumer places a corresponding foot onto the scanner in registration with the projected foot image thereby locating the foot in a semi-weighted supported position. Process 33 then scans the foot to produce an array of measurements representing the topography of the bottom of the consumer's foot. Process 34 converts that array of measurements into a data file for further processing. Process 35 produces an output image and other information for the consumer. Processes 32 through 35 are repeated for the consumer's other foot.

Process 36 uses the information from both feet to identify components for the footbeds and provides a list of those components. Process 37 represents the production-delivery phase during which the consumer obtains the identified components from the local inventory. The consumer then can easily assemble the components into footbeds that closely approximate ideal footbeds for the consumer.

As will be apparent, all the data processing occurs at the local site. As will also become evident, the consumer can be simply directed or guided through this entire operation without assistance from store personnel or practitioners. Moreover both the measurement phase and the production-delivery phase require only a few minutes to complete. As a result finished footbeds are available to the consumer quickly. The reduction in personnel requirements and the existence of a local inventory of components minimizes the costs associated with the production-delivery phase and enables such a footbed to be provided to the consumer at a reasonable cost.

Kiosk 40

Figure 3:
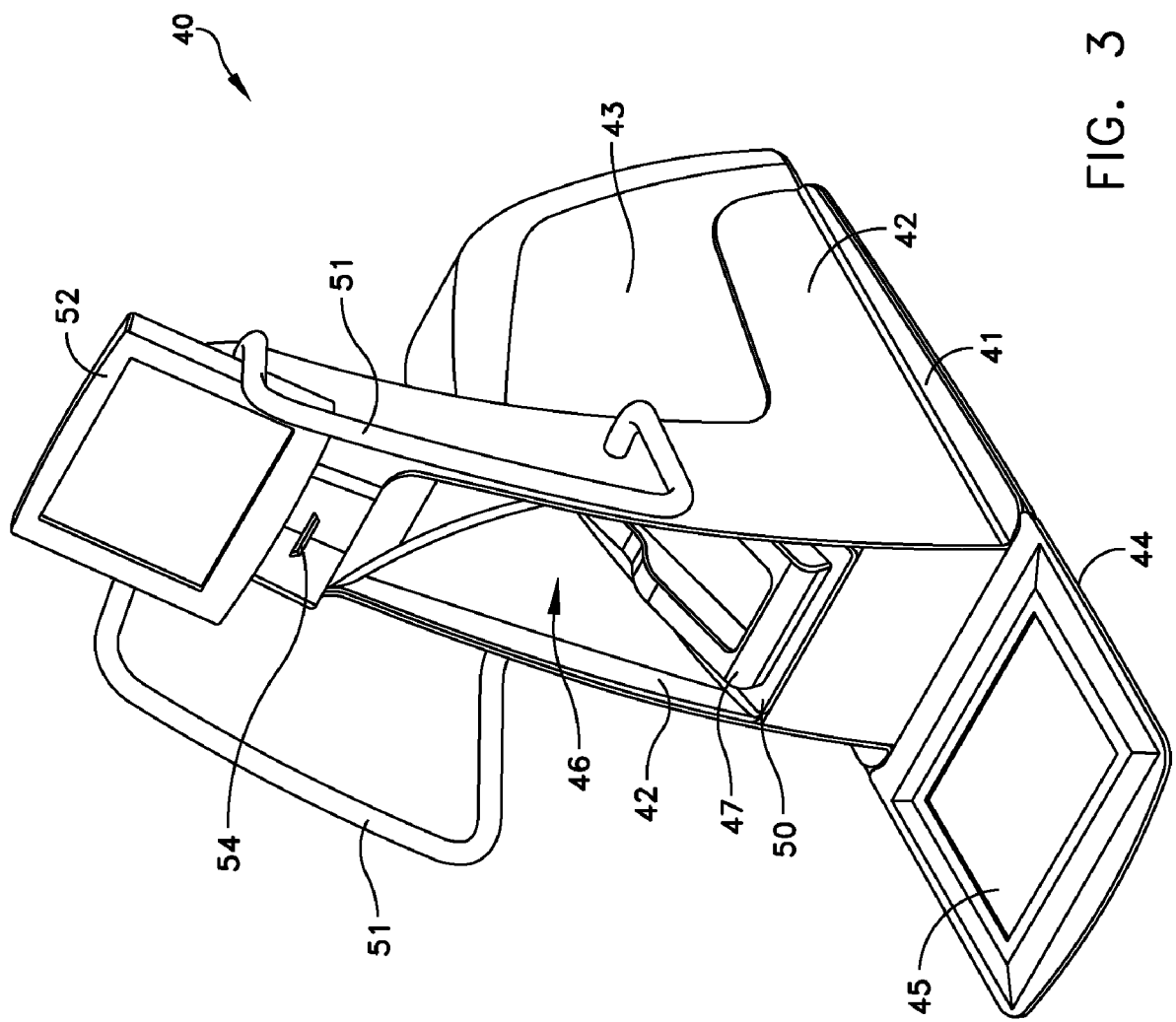
FIG. 3 is a perspective view of a kiosk shown in FIG. 1.
Figure 4:
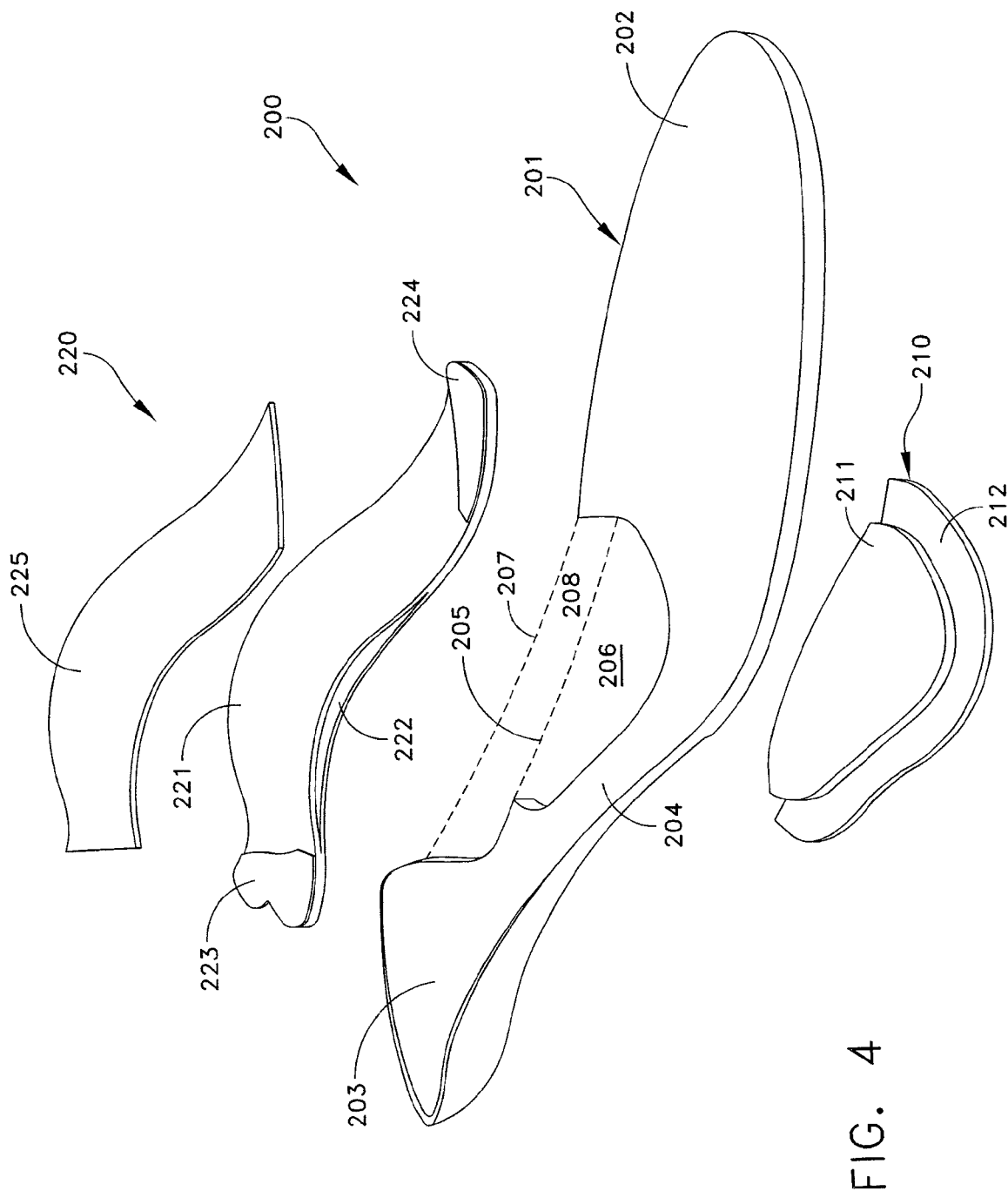
FIG. 4 is an exploded perspective view of components for one embodiment of a right-foot footbed produced in accordance with this invention.
Figure 5:
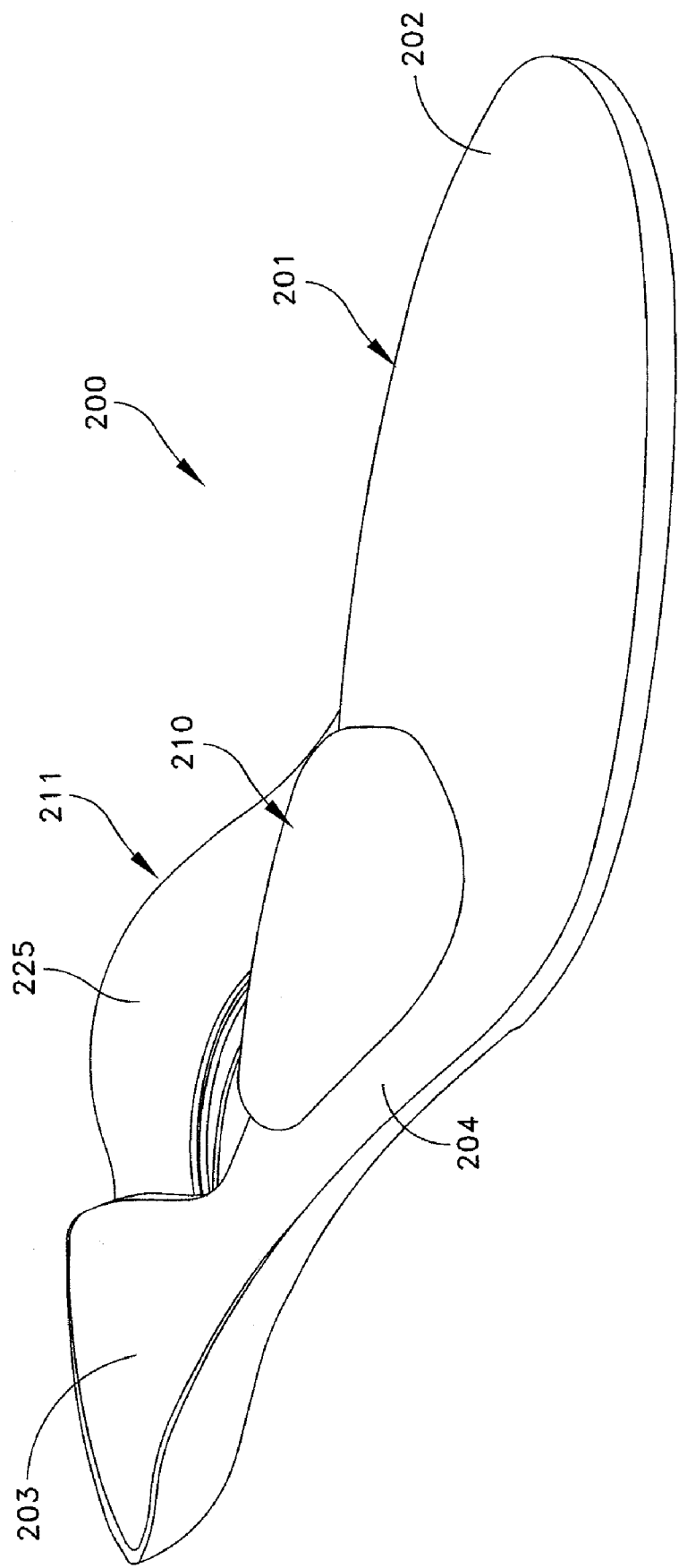
FIG. 5 is a perspective view of a footbed constructed with the components of FIG. 4 in accordance with this invention.

The measurement phase involves interaction between the consumer and a kiosk 40 shown in FIG. 1 and in greater detail in FIGS. 3 through 5. One such kiosk 40 includes a base 41 and a frame 42 with an enclosing housing 43 that opens to the front. In this implementation a detachable base extension 44 extends forward from the base 41 and contains and supports a pressure sensing mat 45. The pressure sensing mat 45 provides a continuous, relatively thin surface that measures distributed pressures along its contact surface. As an output the pressure sensing mat 45 produces an array of pressure signals that are used to produce a pressure map. Such a map shows distributed contact pressures either as a 3D contour map or a 2D color map. While a variety of different pressure sensors can be utilized, it has been found that a pressure mat with a resolution of about 10 mm×10 mm and a full area scan rate of about 10 Hz provides adequate spatial and temporal resolution. Such pressure mats are available from a number of commercial dealers, such as Pressure Profile Systems.

The frame 42 and housing 43 define a cavity 46 that carries a foot pillow assembly 47 based upon the pillow assembly shown in U.S. Pat. No. 7,392,559 In this kiosk 40, the foot pillow assembly 47 resides on a base 50 that elevates the toe portion above the heel portion at an angle that minimizes the consumer's physical exertion and effort in maintaining balance during a scan. Spaced, generally vertically extending parallel handle bars 51 attached to the frame 42 assist the consumer in maintaining balance.

Still Referring to FIG. 3, a consumer who is standing on the pressure mat 45 can easily interact with a touch screen monitor 52 that constitutes an input-output device for a computer (not shown). A printer 54 positioned below the touch screen 52 provides a hard copy output. Detailed operation of the kiosk is described in the above-identified co-pending U.S. patent Ser. No. 11/887,186.

Footbed and Components—Alternative 1

As shown particularly in FIGS. 4 and 5, a footbed 200 in accordance with one embodiment of this invention includes an insole base 201 with portions underlying a consumer's right foot. These include a forefoot portion 202, a rear foot portion 203 and a connecting member 204 between the forefoot portion 202 and the rear foot portion 203. The rear foot portion 203 includes a cup-shaped heel structure for supporting and containing the consumer's heel and related tissue. The connecting member 204 is coextensive with a portion of the lateral column. This structure forms a two-part vacuity. A dashed line 205 in FIG. 4 depicts a medial boundary of a first part 206 that is positioned to underlie the second, third and fourth metatarsals. A dashed line 207 extending from the medial edges of the insole base 201 defines a second part 208 of the vacuity that underlies the arch.

The insole base 201 typically is made of foam such as ethyl-vinyl-acetate or polyurethane. Material properties of the foam may be sport specific. For example, softer and elastic foam may be selected for running; harder and viscous foam, for cycling or soft and viscous foam for golf. In this particular implementation these activities are used to select either a "dynamic" or a "static" footbed insole base 201. That is, a consumer's selection of walking, running or golf causes the system to select a dynamic insole base while the selection of cycling, skating and skiing causes the system to select a static insole base. Other combinations are also possible.

FIGS. 4 and 5 depict a metatarsal pad insert 210 that includes a foam pad 211 affixed an attachment layer 212. The foam pad 211 is formed with a periphery to correspond to part 206 of the vacuity. That is, the foam pad 211 fills the vacuity part 206 when the underlying layer 212, that includes hook and loop portions as an example, attaches to corresponding hook and loop surfaces on the bottom of the insole base 201.

The final component is an arch support insert 220 shown in each of FIGS. 4 through 7. The arch support 220 has a curved upper portion 221 and an essentially flat lower portion 222 that are joined at the ends. The curved upper portion is flexible in three dimensions and is typically made of a plastic, such as polyether block amide sold under the trademark Pebax® owned by Arkema, a French corporation or a thermo-plastic urethane. Curved upper portion 221 forms an arch to accommodate the human medial arch. As the upper portion is flexible in three dimensions, it can adjust to height, length and shape of the foot arch. The lower part 222 is essentially flat and stiff. It includes portions 223 and 224 containing hook and loop material that attaches to corresponding material on the underside of the insole base 201. A layer 225 of soft foam overlies the upper portion 221 to provide physical comfort.

Figure 6:
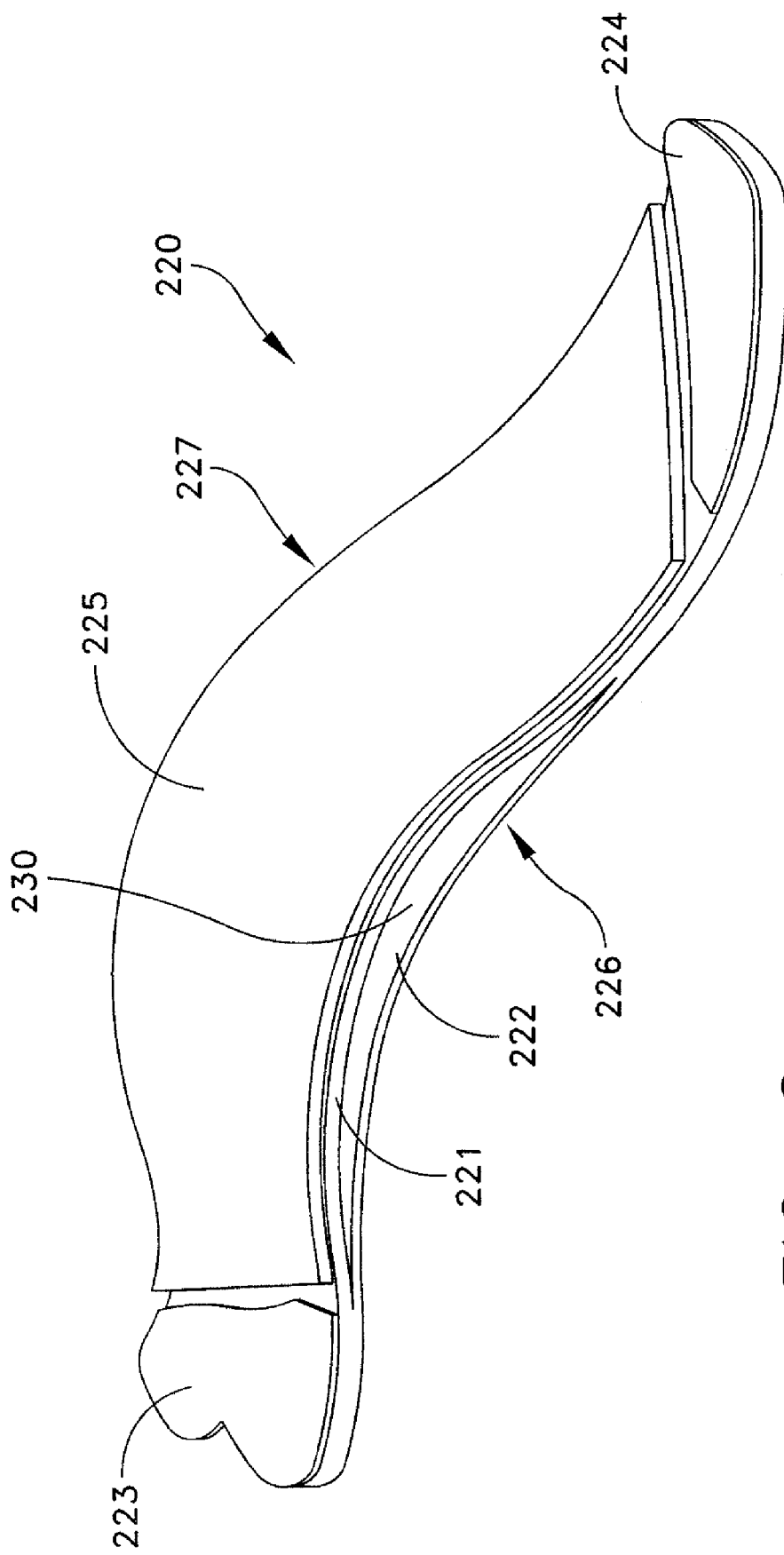
FIG. 6 is a perspective view of an arch support insert component taken from one side.
Figure 7:
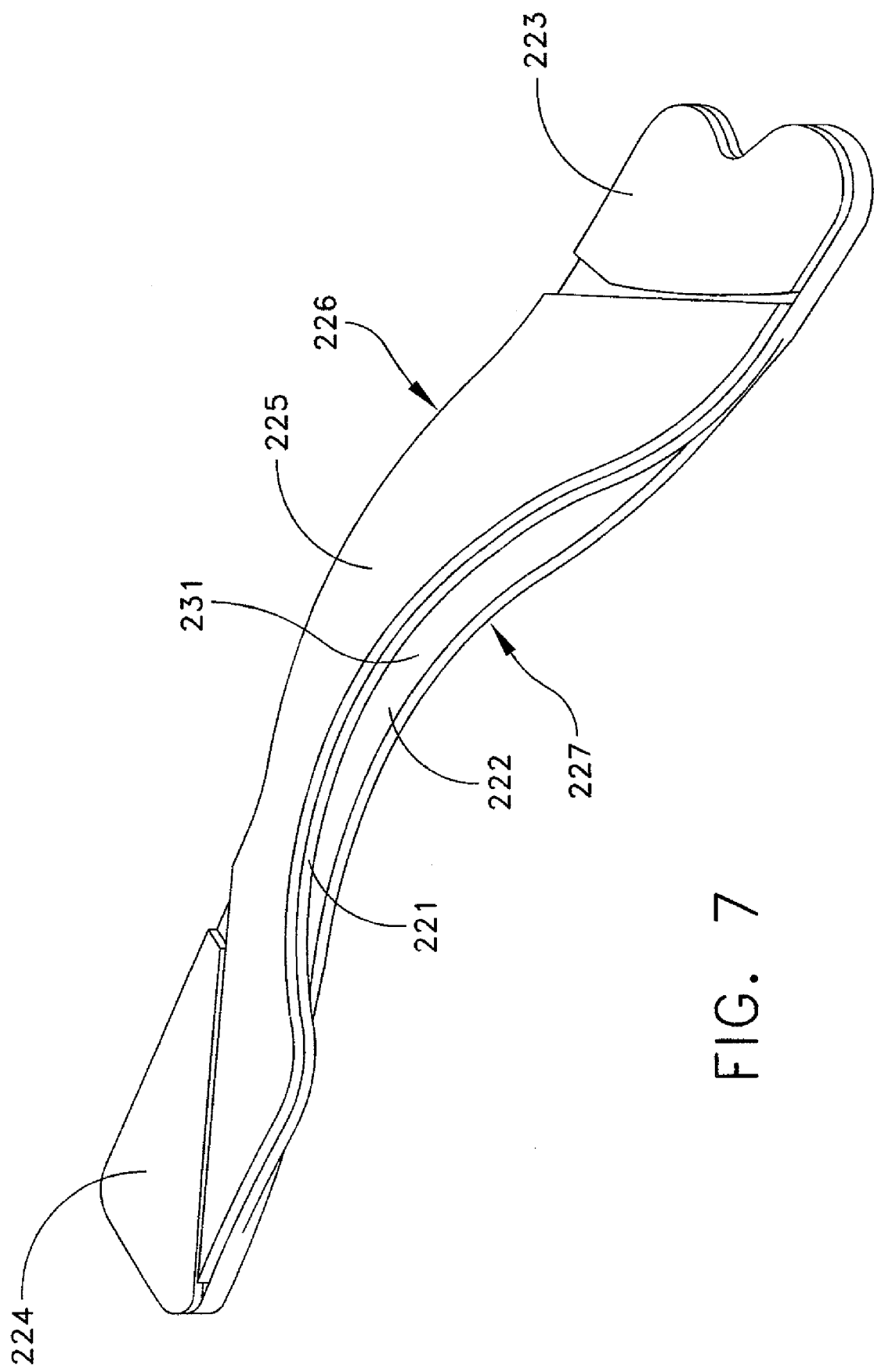
FIG. 7 is a perspective view of an arch support insert component taken from other side.

Referring specifically to FIGS. 6 and 7, a finished arch support insert 220 has a medial edge 226 and a lateral edge 227. FIG. 6 is a perspective view from the medial edge 226; FIG. 7, from the lateral edge 227. The curved support portion 221 and layer 225, attached at the ends thereof to the lower part 222, cant from a minimum separation from the lower part 222 at the medial edge 226 to a maximum at the lateral edge 227. This cant facilitates the fit between the consumer's arch and the layer 225. The lower part 222 further prevents the upper part 221 from flattening during use.

FIG. 8 is useful in understanding a range of variations that can be achieved by combining the component shown in FIGS. 4 and 5. Specifically, FIG. 8 depicts two insole bases 201A and 201B in a group of the same size. For example, the insole base 201A is in a subgroup constructed for static use; the insole base 201B, in a subgroup for dynamic use. Two metatarsal pad inserts 210A and 210B are in a group for a given insole base size that includes at least two subgroups. As shown in FIGS. 8 and 9, the metatarsal pad insert 210A has a relatively flat foam pad 211A and is in a first subgroup; the metatarsal pad insert 210B, as shown in FIGS. 8 and 10, has a rounded and thicker foam pad 211B and is in the second subgroup. The shapes of the metatarsal pad inserts for each subgroup are shown in FIG. 8. FIG. 8 also depicts a group of arch support inserts 220A, 220B and 220C that provide support for high, medium and low arches subgroups, respectively.

Figure 12:
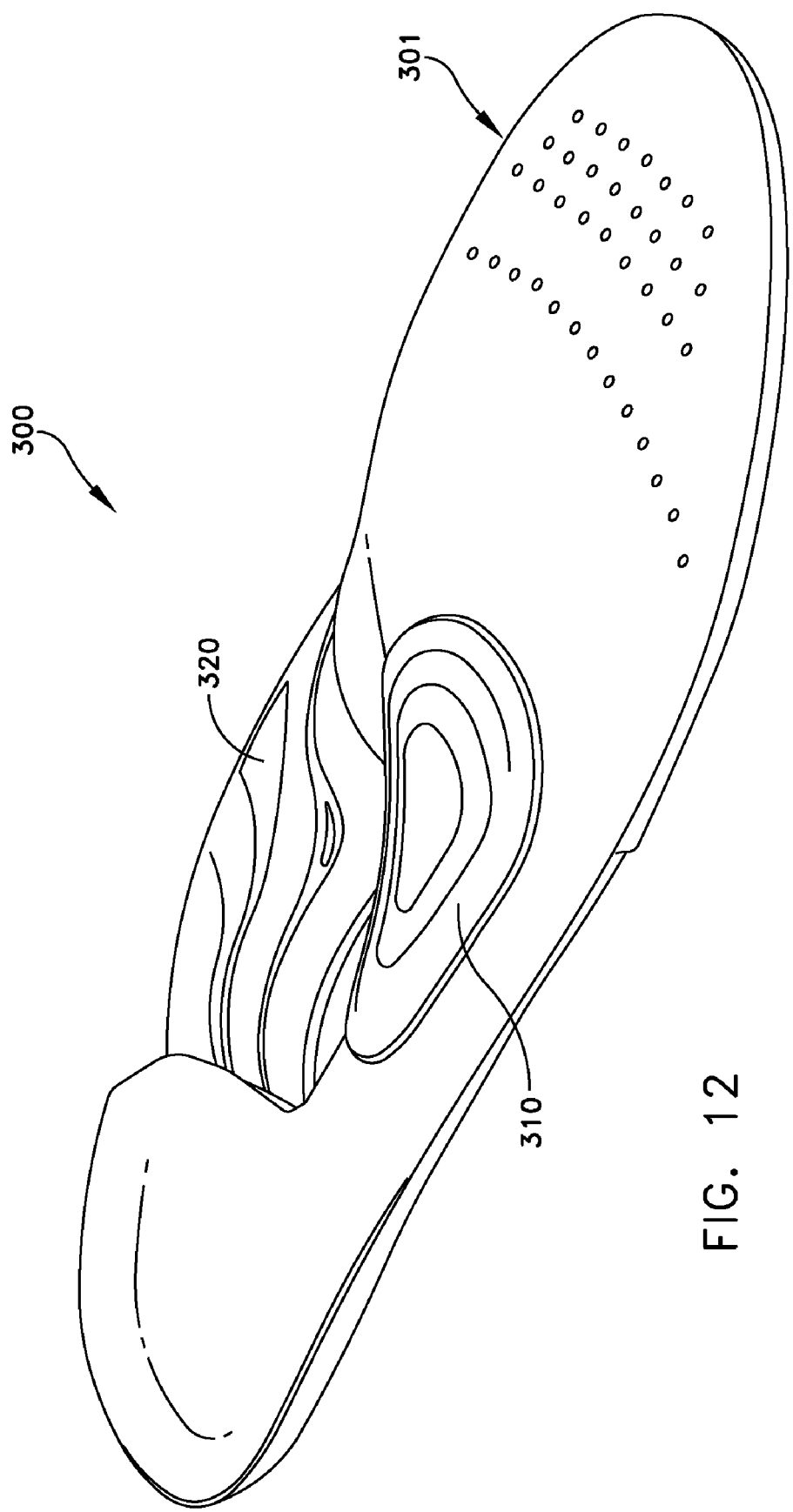
FIG. 12 is a perspective view of another embodiment of a footbed for a right foot that incorporates this invention and that includes an insole base, an arch support and a metatarsal pad.

With this range of components, it will be apparent that the materials of the insole base 201 in FIG. 12 can be varied for different applications. The metatarsal pad insert 210 can be modified to provide different support functions. The arch support insert 220 can be selected to provide different elevations for arch support. In this specific example, a combination of a component from selected subgroups enables a given footbed to have one of twelve variations.

As previously indicated, the system of this invention assumes that at each kiosk location there will be a matrix of components such as shown in FIG. 8 that can be assembled into any of the wide variety of footbeds for shoes. As shown in FIG. 11, in one particular embodiment, the inventory covers shoe sizes from 3.5 to 13. It has been found by analyzing thousands of images obtained by means of the apparatus and procedure shown U.S. Pat. No. 7,392,559 that one group of insole bases 201 can be sized to accommodate two shoe half sizes. Consequently, the inventory only requires ten pairs of insole bases lengths for a range of twenty half-shoe sizes. This number will be multiplied further by the different types of materials used in the insole bases 201; for example, twenty pairs of insole bases if there are static and dynamic footbeds. Likewise, using the system of FIG. 11 as the model, it has been found that each group of arch support inserts 220 and each group of metatarsal pads 210 will span four half sizes. That is, there is a requirement of a total of ten pairs of metatarsal pads if two thicknesses are available. There will be a total of fifteen pairs of arch support inserts assuming that there are three arch heights.

Footbed and Components—Alternative 2

FIGS. 12 through 26 depict an alternate embodiment of a footbed 300 and components for a consumer's right foot. A footbed for the left foot will be a mirror image and is therefore not disclosed; its construction will be obvious to those of ordinary skill in the art.

More specifically, FIG. 12 depicts a footbed 300 that includes three basic components, namely: an insole base 301, a metatarsal pad insert 310 and an arch support insert 320.

Figure 13:
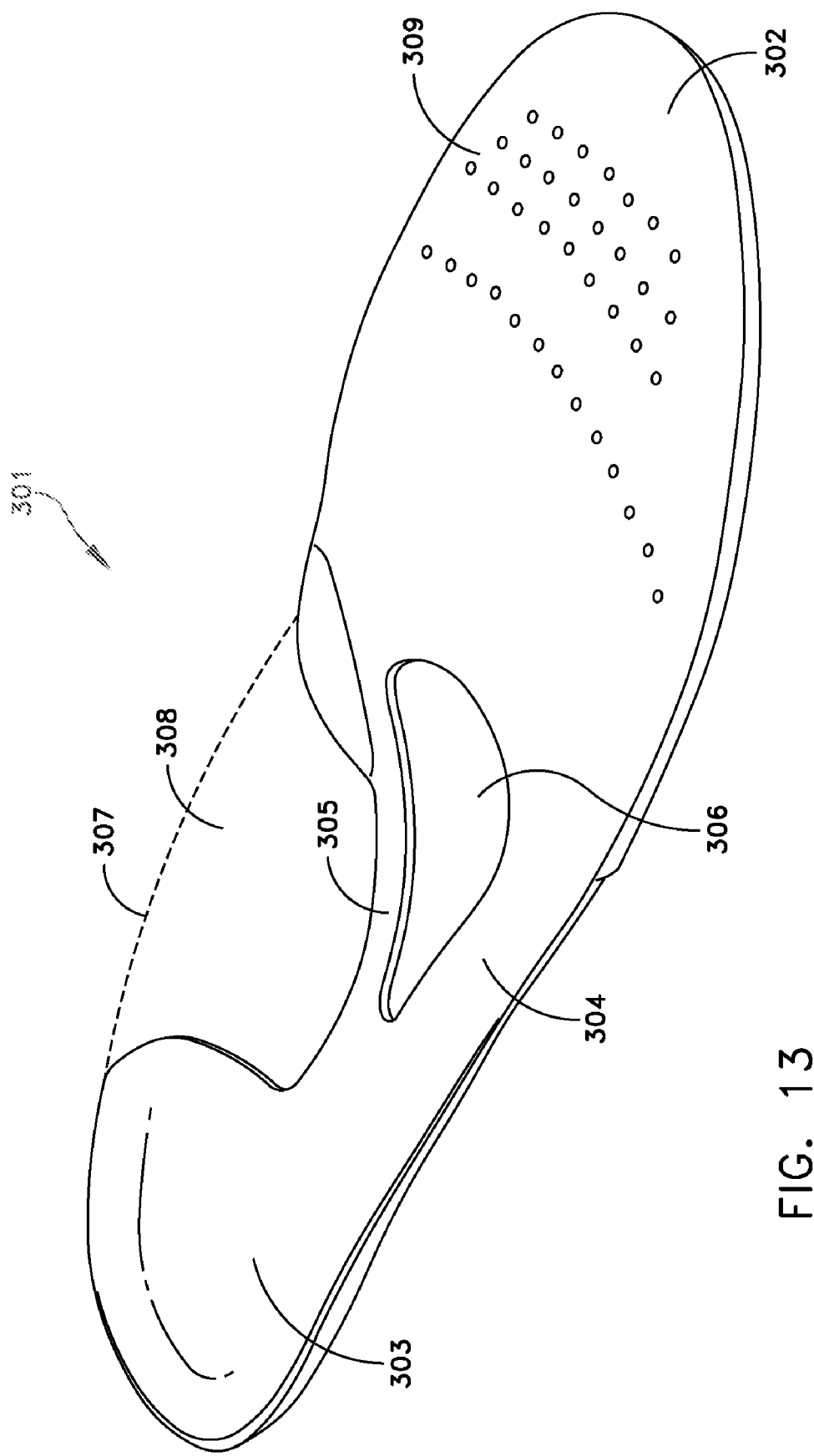
FIGS. 13 through 15 are perspective top and bottom views of an insole base shown in FIG. 13.
Figure 14:
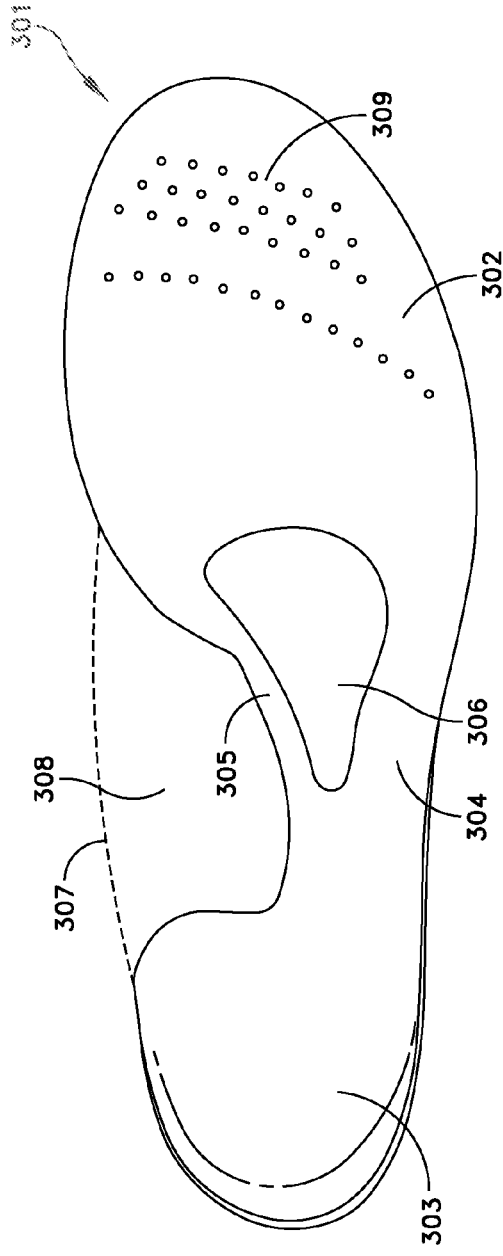
Figure 15:
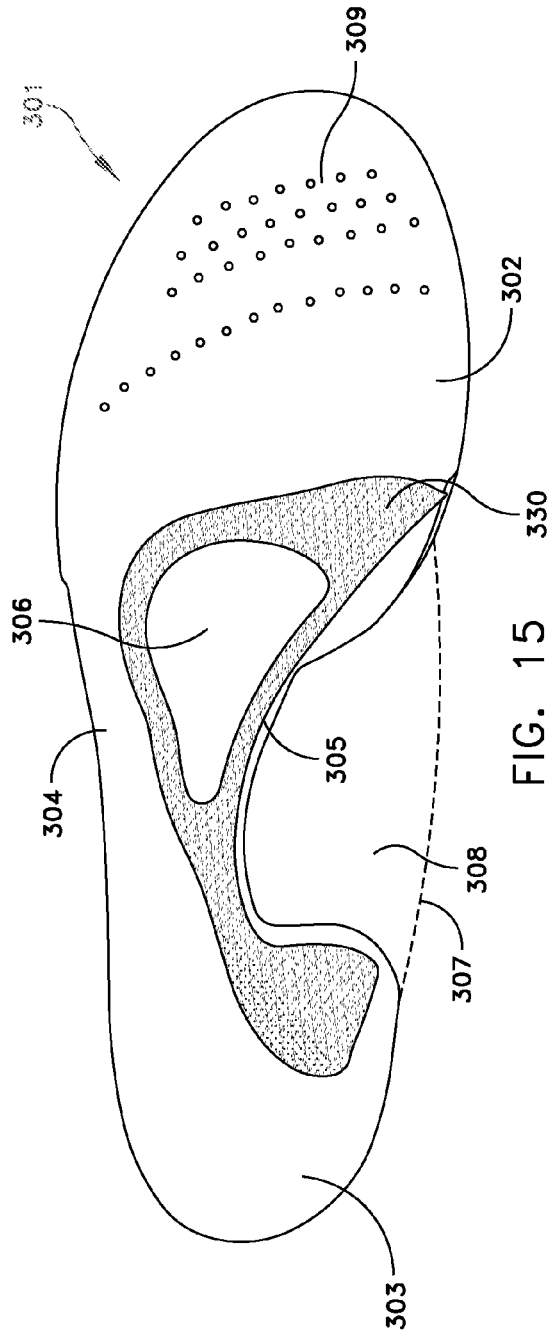

FIGS. 13 through 15 depict respectively a perspective view and top and bottom planar views of the insole base 301, respectively, in which different base portions underlie different portions of the consumer's foot. These include a forefoot portion 302, a rear foot portion 303 and a connecting member 304 between the forefoot portion 302 and the rear foot portion 303. The rear foot portion 303 includes a cup-shaped heel structure for supporting and containing the consumer's heel and related tissue. The connecting member 304 also is coextensive with a portion of the lateral column. This structure forms a two-part vacuity in which a web member 305 constitutes a medial boundary for a metatarsal pad insert vacuity 306 that is positioned to underlie the consumer's second, third and fourth metatarsals. A dashed line 307 extends from the medial edges of the insole base 301 to define, with the web member 305, the boundaries for an arch support insert vacuity 308 that underlies the consumer's arch.

As in the first embodiment, the insole base 301 typically is made of foam such as ethyl-vinyl-acetate or polyurethane and may be sport specific. The web member 305 improves dimensional stability for the insole member 301 and stabilizes the peripheries of the vacuities 306 and 308. As described later, the web member 305 also enhances the reliability of the attachment mechanism that maintains the components as a unitary structure during use.

The insole base 301 also includes an array of apertures or perforations 309. The perforations 309 improve the flexibility of the forefoot portion 302, minimize weight and provide breathing for comfort.

Figure 16:
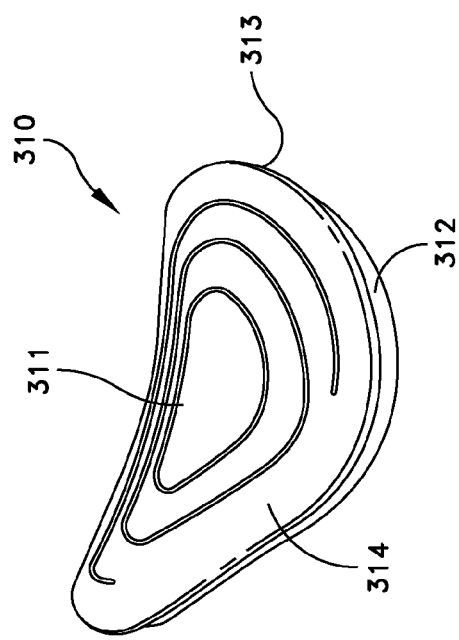
FIGS. 16 through 18 are perspective, top and bottom views of a metatarsal pad for use in a footbed produced in accordance with this invention.
Figure 18:
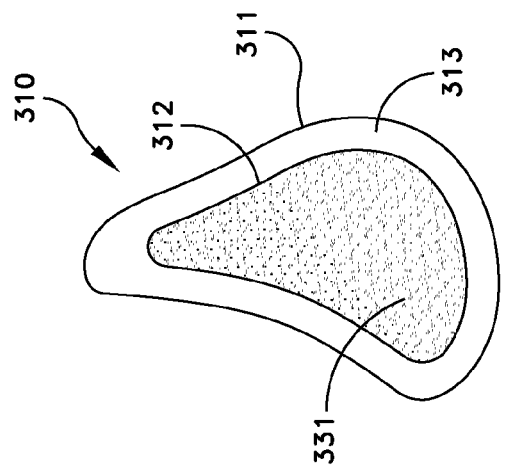
Figure 17:
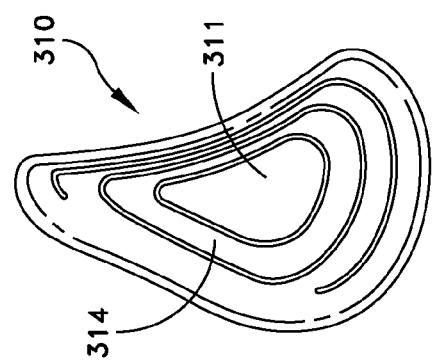

FIGS. 16 through 18 are respectively perspective and top and bottom planar views of a metatarsal pad insert 310. In this embodiment the metatarsal pad insert 310 comprises an integrally molded pad body 311 and depending insert extension 312. The depending insert extension 312 is shaped with a periphery that substantially matches the periphery of the metatarsal pad insert vacuity 306 and locates the metatarsal pad insert 310 with respect to the insole base 301 of FIGS. 13 through 15. The pad body 311 overlies and extends beyond the depending insert 312 to form a peripheral shoulder 313. Consequently when inserted into the vacuity 306 of FIG. 13 the metatarsal pad insert 310 is seated. A top surface 314 of the metatarsal pad insert 310 is rounded to be thicker at the center and thinner at the periphery to conform to the topography of the consumer's foot under the metatarsals. In a preferred embodiment the metatarsal pad can be molded from EVA, urethane or other like plastic materials.

Figure 19:
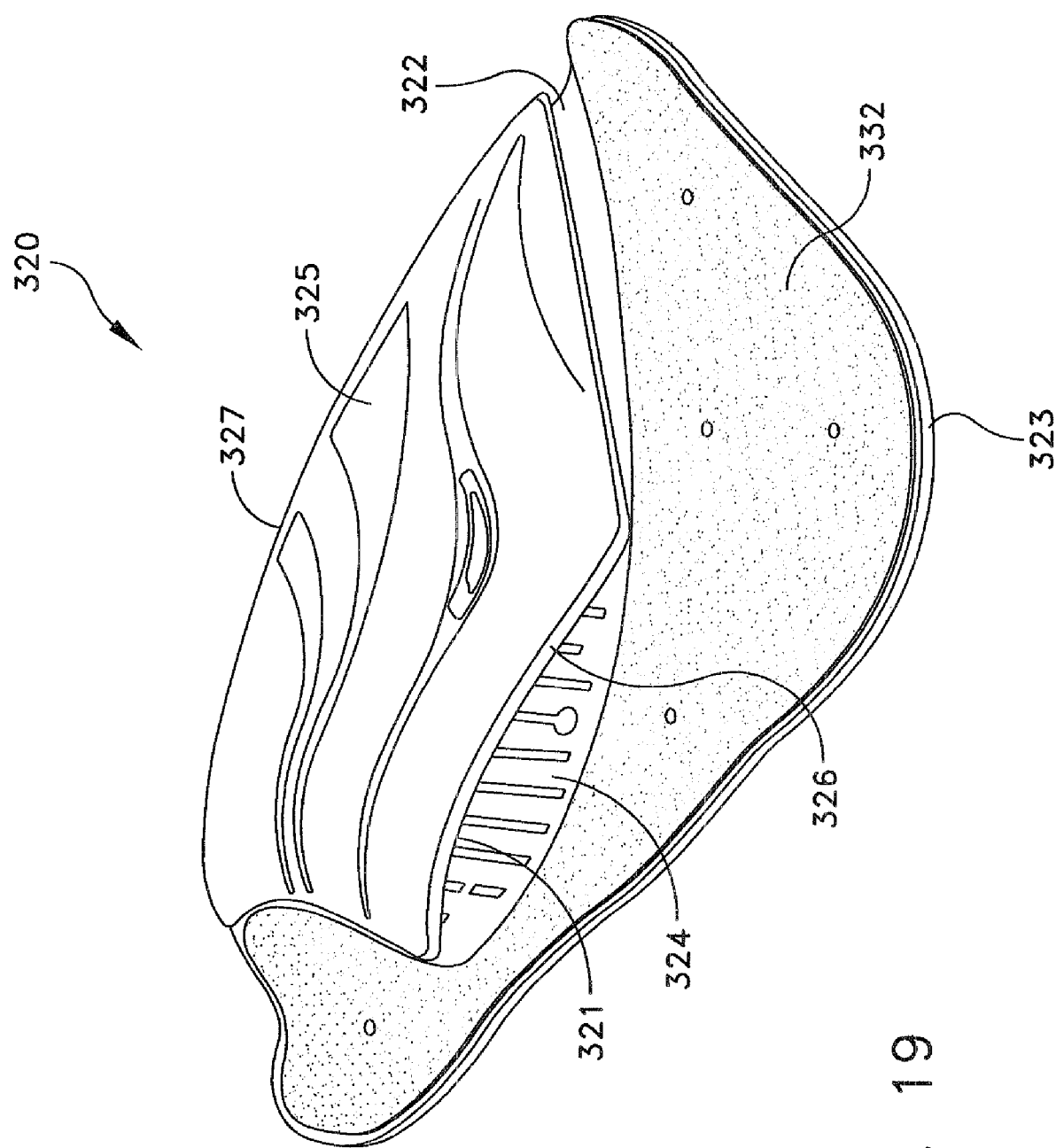
FIGS. 19 through 21 are perspective and planar views of different aspects of an arch support structure in accordance with this invention.
Figure 20:
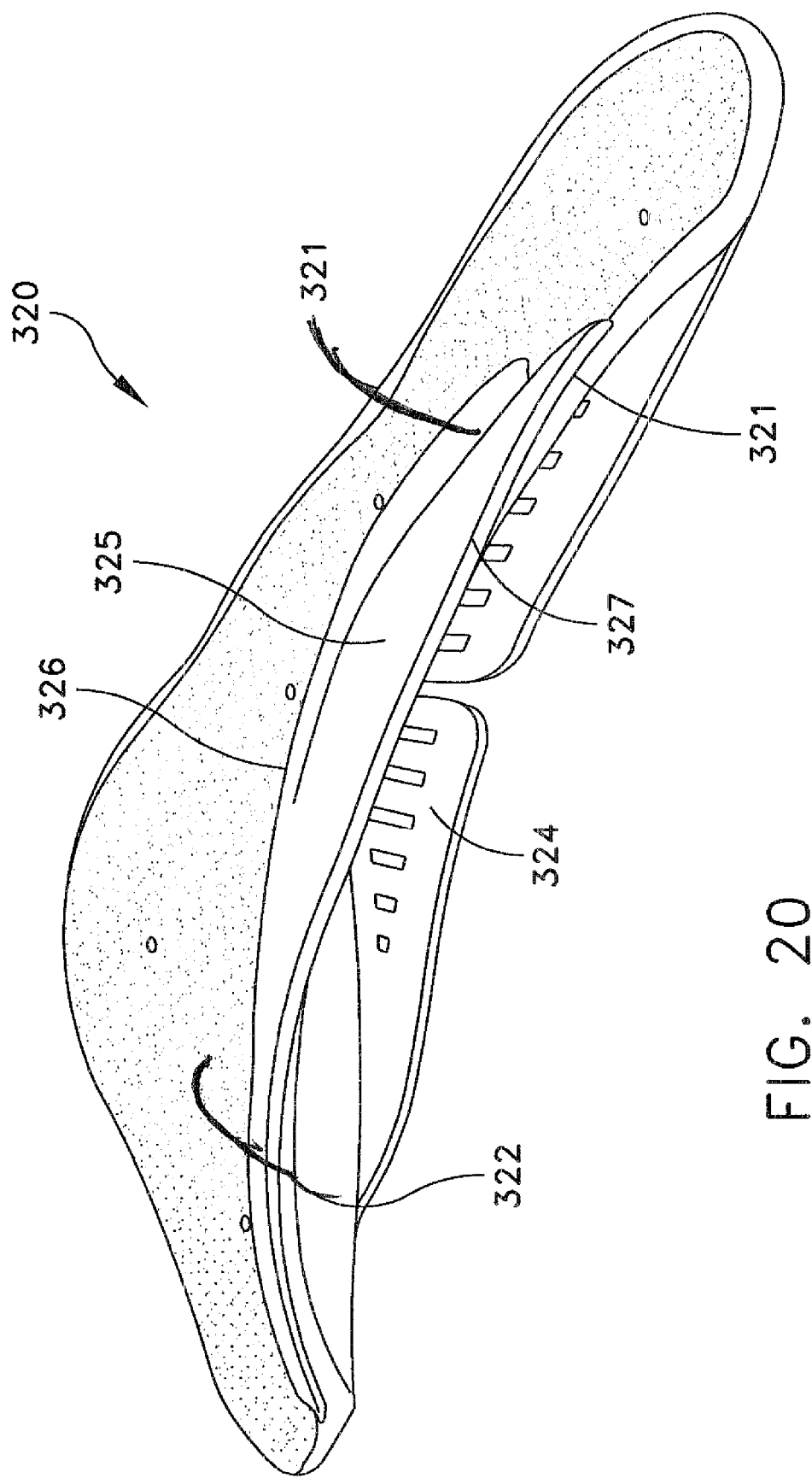
Figure 21:
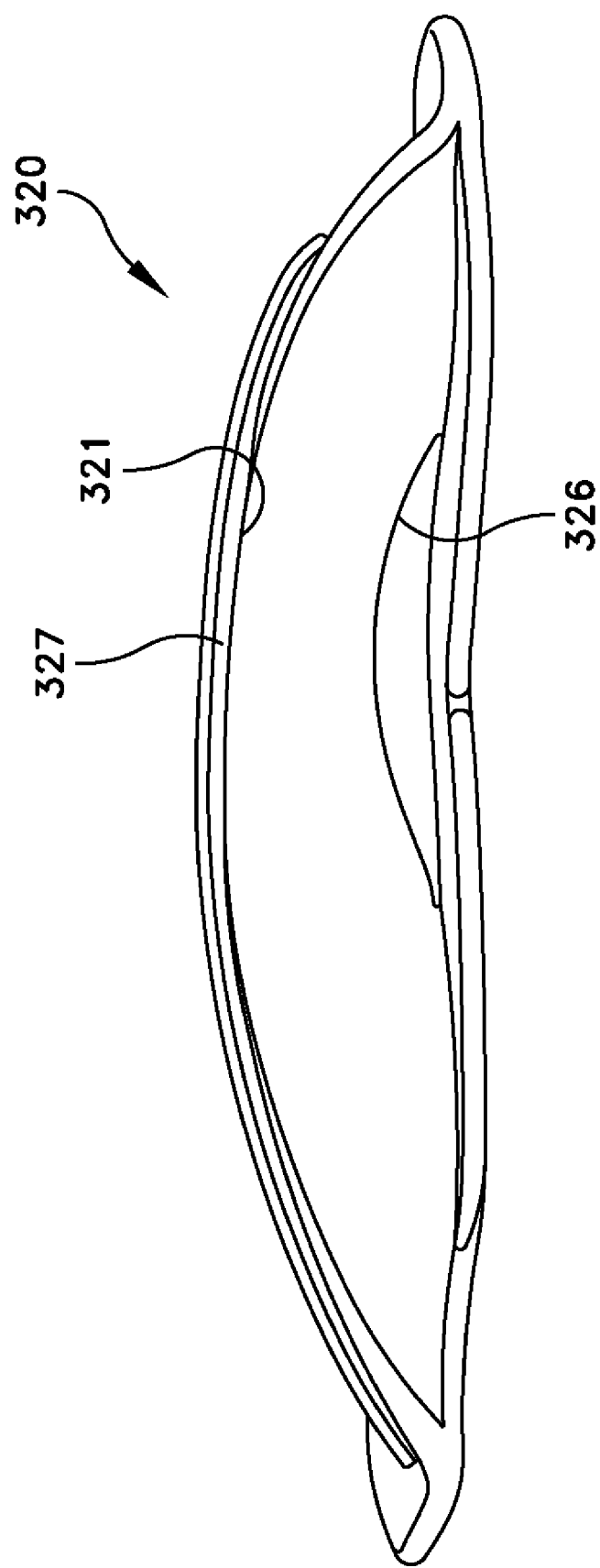

FIGS. 19 through 21 depict an arch support insert 320 that includes a curved upper portion 321 and a base 322. The arch support insert 320 can also be integrally molded of a plastic, such as polyether block amide sold under the trademark Pebax® owned by Arkema, a French corporation or other thermo-plastic urethane.

A first portion 323 of the base 322 is shaped to underlie the metatarsal pad insert vacuity 306 and web 305 of FIG. 13 and to conform to the general contour that the bottom surface of the insole base 301. A second portion 324 of the base 322 extends laterally from the first portion 323 to underlie a portion of the arch insert vacuity 308 adjacent the web 305. The second portion 324 has a plurality of spaced, parallel closed and open ended slots. The ends of the curved upper portion 321 are integral with both the first and second portions 323 and 324. This structure permits limited three-dimensional flexure of the curved upper portion 321. Consequently the curved upper portion 321 accommodates the consumer's medial arch. That is, it can adjust to height, length and shape of the consumer's foot arch as the consumer applies weight. When the consumer removes a shoe, the curved upper portion 321 returns to its original shape due to the release of stresses introduced into the arch support insert 320 during use.

A layer 325 of soft foam or elastomeric material may overlie the curved upper portion 321 to provide physical comfort.

Referring specifically to FIGS. 20 and 21, a finished arch support insert 320 according to this embodiment has a medial edge 326 and a lateral edge 327. The curved upper portion 321 and layer 325, attached at the ends thereof to the second portion 324, cants from a minimum separation from the lower part 324 at the medial edge 326 to a maximum at the lateral edge 327. This cant facilitates the fit between the consumer's arch and the layer 325. This structure also prevents the curved upper portion 321 from flattening during use thereby to maintain its arch support function.

The description of subgrouping of components and the inventory as described earlier with respect to FIGS. 8 through 11 is equally applicable to an insole having the construction as described with respect to FIGS. 12 through 21. As true with respect to the first embodiment with the assembly of components such as those shown in FIGS. 8 through 10, the components shown particularly the insole base 301, the metatarsal pad insert 310 and the arch support insert 320 in FIGS. 13, 16 and 19, respectively, are also assembled by complementary, releasable, attachment structures.

A particularly useful releasable attachment structure is constituted by hook and loop material. As will become apparent from the following discussion, the material attached to the first one of the complementary releasable structures (e.g., the loop material) is formed with the insole insert and metatarsal pad insert while the other complementary material (e.g., the hook material) is applied to the arch support insert. The outer shape of the loop material 330 essentially conforms to the shape of the first portion 323 of the arch support insert 320 as shown in FIG. 19. Loop material 331 is also applied to the bottom surface of the depending insert portion 312 as shown in FIG. 18. The other of the complementary attachment structures is applied to the first portion 323 of the arch support insert 320 as designated by reference numeral 332 in FIG. 19.

Figure 22:
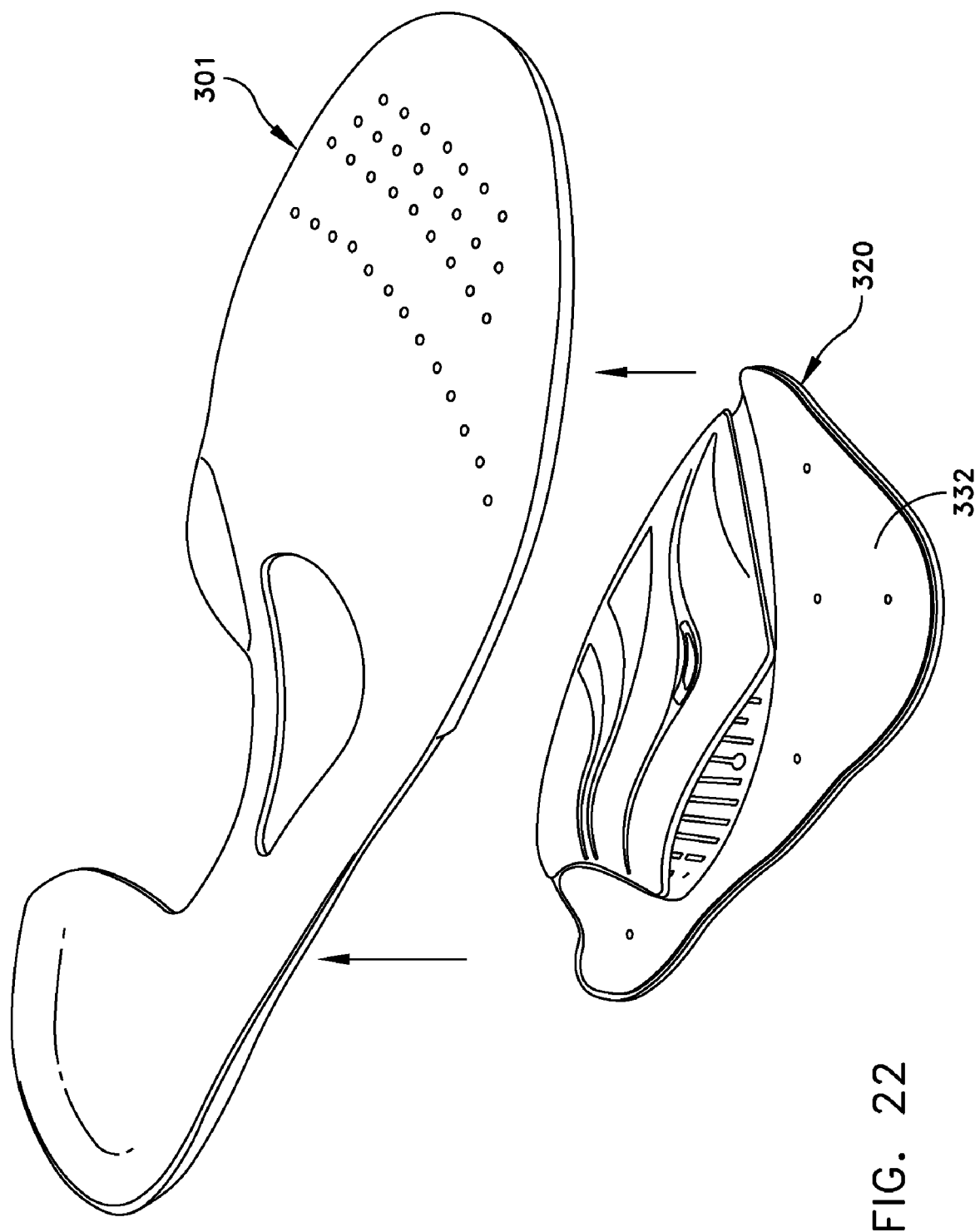
FIG. 22 depicts the relationship between an insole base member as shown in FIGS. 13 through 15 and an arch support as shown in FIGS. 19 through 21 for assembly.
Figure 23:
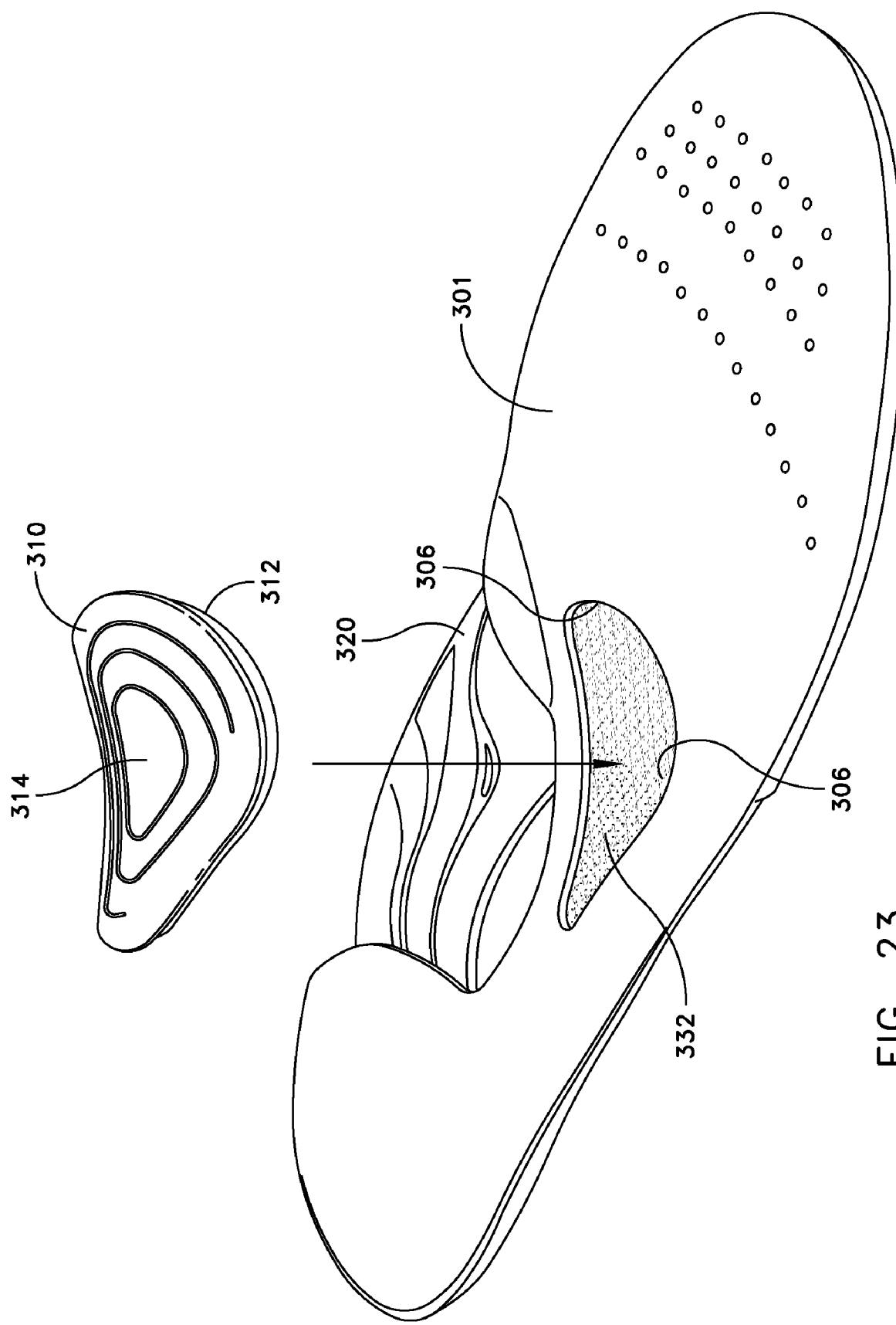
FIG. 23 depicts the relationship of the metatarsal pad such as shown in FIGS. 16 through 18 to the combination of the assembled insole base and arch support in accordance with FIG. 25 for assembly into the final footbed sown in FIG. 12.

For assembly, a consumer first attaches the selected arch support insert 320 to the bottom of the selected insole base 301 whereupon the hook material 332 on the arch support insert engages the loop support material 330 on the insole base 30, not shown in FIG. 22, but shown in FIG. 15. During assembly of this element, alignment is facilitated by the corresponding outlines of the loop material 330 in FIG. 15 and the outline of the arch support insert 320 shown in FIG. 22. When this step is complete, there is a subassembly as shown in FIG. 23. With this subassembly, the arch support insert 320 is fixed to the bottom of the insole base 301. The hook material 332 on the arch support 320 is exposed through the vacuity 306.

Now the consumer aligns the metatarsal pad insert 310 with the top surface as shown in FIG. 23 such that the pending insert portion 312 enters the vacuity 306 and the loop material 331 engages the hook material 332. When this has been completed, the result is the footbed 300 shown in FIG. 12.

After the components have been assembled into the footbed 200 of FIG. 5 or the footbed 300 of FIG. 12, the consumer inserts each into the corresponding footwear. Then the consumer can don his or her footwear.

As known, during locomotion an individual's arch varies dynamically in length and height. A fixed arch support can not accommodate these changes. However, arch support inserts like the arch support inserts 220 of FIGS. 6 and 320 of FIG. 19 that incorporate this invention have certain characteristics that improve and maintain proper arch support during consumer locomotion. As previously indicated, the curved upper portions 221 in FIGS. 6 and 321 in FIG. 19 can undergo limited three-dimensional flexure in substantial isolation from their respective bases 222 and 322. As a result, during locomotion, the flat lower portions or bases 222 and 322 maintain contact with the sole of the shoe. At the same time, the curved upper portions 221 and 321 can move in response to natural changes in arch height and length. Thus, proper arch support is maintained even as the consumer's arch shape changes during locomotion.

In summary, the two alternative embodiments of footbeds provide a consumer with footbed components that are readily assembled into a footbed. Each embodiment meets the various objectives of this invention. Each embodiment provides a high quality footbed at a low cost because the individual components, having a finite inventory, can be mass produced. In each embodiment a consumer can easily assemble the selected components to produce a footbed. The construction of each embodiment enables the construction of a footbed with minimal cost associated with measurement and production-delivery phases and permits the selection of components by means of measurements that can be accomplished by a consumer without assistance.

This invention has been described in terms of a specific implementation with reference to specific variations. It will be obvious to those of ordinary skill in the art that myriad variations and modifications could be made to this specifically disclosed implementation without departing from the spirit and scope of this invention. Therefore, it is the intent of the appended claims to cover all such variations and modifications as come within the true spirit and scope of this invention.

What is claimed as new and desired to be secured by Letters Patent of the United States is:

1. A footbed for an individual's foot characterized by forefoot, rear foot, lateral and medial column, arch and metatarsal head areas, said footbed comprising:
   A) an insole base taken from a group of insole bases for underlying the forefoot and rear foot areas and portions of the lateral column area between the forefoot and rear foot areas, each said insole base having at least one vacuity substantially coextensive with the areas underlying the arch and metatarsal head areas and portions of the medial column area,
   B) a metatarsal pad insert taken from a group of metatarsal pad inserts of different properties,
   C) an arch support insert taken from a group of arch support inserts of different properties, each said arch support insert including:
      i) a curved flexible upper portion that forms an arch for accommodating the individual's medial arch,
      ii) a flat stiff lower portion attached to the ends of said upper portion thereby to stabilize said upper portion, said lower portion being attached to ends of said upper portion and extending beyond the end of said upper portion, and
   D) means for attaching said metatarsal pad and arch support inserts to said insole base to span said at least one vacuity for providing support for the metatarsal head and arch areas of the foot, respectively, wherein the extension of said lower portion includes an element of said attachment means.

2. A footbed as recited in claim 1 wherein said attachment means includes hook and loop material attached to the underside of said insole base adjacent said vacuity and to the periphery of said metatarsal pad insert and the ends of said arch support insert.

3. A footbed as recited in claim 1 wherein said attachment means includes complementary hook and loop strips, one of said hook and loop strips being attached to the underside of said insole member adjacent said vacuity and the other of said hook and loop strips being attached to each of said metatarsal pad and arch support inserts.

4. A footbed as recited in claim 1 wherein said metatarsal head vacuity is coextensive with the position of the 2nd, 3rd and 4th metatarsals.

5. A footbed as recited in claim 1 wherein said insole base includes an integral web that divides the at least one vacuity into a metatarsal vacuity for alignment with the 2nd, 3rd and 4th metatarsals and an arch vacuity for alignment with the arch.

6. A footbed as recited in claim 5 wherein said attachment means includes first attachment means on said insole base adjacent said vacuities and each of said metatarsal pad insert and complementary second attachment means on said arch support.

7. A footbed as recited in claim 1 wherein said metatarsal pad insert comprises an integrally molded base and pad wherein the periphery of said insole base extends beyond the periphery of said pad and wherein said first attachment means is coextensive with at least a portion of the surface of said pad.

8. A footbed for an individual's foot characterized by forefoot, rear foot, lateral and medial column and arch, said footbed comprising:
   A) an insole base taken from a group of insole bases for underlying the forefoot and rear foot areas and portions of the lateral column area between the forefoot and rear foot areas, said insole base having a vacuity substantially coextensive with the area underlying the arch area and portions of the medial column area,
   B) an arch support insert taken from a group of arch support inserts of different properties, said arch support insert being integrally molded and including:
      i) a curved resilient arch supporting portion having a height for accommodating the individual's medial arch, and
      ii) a base that conforms substantially to the bottom of said insole base and that supports said arch supporting portion in said vacuity thereby to stabilize said arch supporting portion, and
   C) means for attaching said arch support insert to said insole base to span at least said vacuity for providing support for the arch area of the foot.

9. A footbed as recited in claim 8 wherein said attachment means includes hook and loop material attached to the underside of said insole base adjacent said vacuity and to the ends of said arch support insert.

10. A footbed as recited in claim 8 wherein said attachment means includes complementary hook and loop strips, one of said hook and loop strips being attached to the underside of said insole member adjacent said vacuity and the other of said hook and loop strips being attached to the arch support inserts.

* * * * *